| United States Patent [19] | [11] | 4,067,968 |
|---|---|---|
| Lazzari et al. | [45] | Jan. 10, 1977 |

[54] DAUNOSAMINE NUCLEOSIDES

[75] Inventors: Ettore Lazzari; Federico Arcamone; Aurelio di Marco, all of Milan, Italy

[73] Assignee: Societa Farmaceutici Italia S.p.A., Milan, Italy

[21] Appl. No.: 746,851

[22] Filed: Dec. 2, 1976

[30] Foreign Application Priority Data

Dec. 18, 1975    United Kingdom ............... 51967/75

[51] Int. Cl.$^2$ ...................... A61K 31/70; C07H 19/06; C07H 19/16
[52] U.S. Cl. .................................... 424/180; 536/23; 536/24; 536/26
[58] Field of Search ............................. 536/23, 24, 26; 424/180

[56] References Cited

U.S. PATENT DOCUMENTS

| 3,654,262 | 4/1972 | Walton .................................. 536/24 |
| 3,721,664 | 3/1973 | Hoffer .................................. 536/23 |
| 3,748,320 | 7/1973 | Vorbruggen et al. ................. 536/23 |
| 3,803,124 | 4/1974 | Arcamone et al. .................... 536/17 |
| 3,817,980 | 6/1974 | Vorbruggen et al. ................. 536/23 |

*Primary Examiner*—Johnnie R. Brown
*Attorney, Agent, or Firm*—Hubbell, Cohen, Stiefel & Gross

[57] ABSTRACT

The antitumor efficacy of the known antibiotics daunomycin (daunorubicin) and adriamycin (doxorubicin) is synergized by the use of said antibiotics together with a daunosamine nucleoside. The latter compounds are prepared by condensing a reactive protected daunosamine with a reactive protected heterocyclic base.

7 Claims, No Drawings

DAUNOSAMINE NUCLEOSIDES

BACKGROUND OF THE INVENTION

1. Field of the Invention

The present invention relates to daunosamine nucleosides, their preparation and use.

2. The Prior Art

The compounds of the present invention are condensation products of the known amino sugar - daunosamine, i.e., (3-amino-2,3,5-trideoxy-L-lyxo-hexopyranose), which is also the sugar moiety of the known antibiotics daunomycin and adriamycin and the known purine and pyrimidine bases—adenine, thymine and cytosine. However, in order to make the novel compounds of the inventions, one must use reactive protected derivatives of daunosamine as well as of the heterocyclic (purine or pyrimidine) bases.

Among the reactive protected daunosamines that can be used in the process of the invention there are included 3,4-ditrifluoroacetyl-α-daunosaminyl chloride (Va) which can be prepared as described by Arcamone et al. in a Communication presented at the "Adriamycin, New Drug Symposium", San Francisco, 1975, January 15-16, and 3,4-diacetyl-α-daunosaminyl acetate (Vb) prepared in accordance with the procedure of Arcamone et al in Gazz. Chim. It., 100, 949-989 (1970)

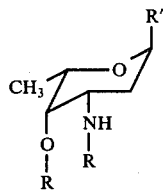

Va R=COCF$_3$; R'=Cl
Vb R=R'=COCH$_3$

SUMMARY OF THE INVENTION

The present invention provides, in one aspect thereof, a new class of compounds which are daunosamine nucleosides, as well as certain novel intermediates used in the preparation thereof. The novel compounds of the invention are those of the formulae (I) through (IV):

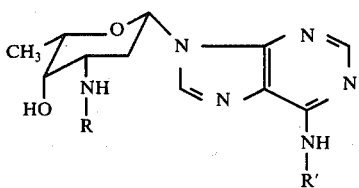

Ia R=R'=H 9-(β-daunosaminyl)-adenine;
Ib R=COCF$_3$; R'=CO—C$_6$H$_5$, protected derivative.

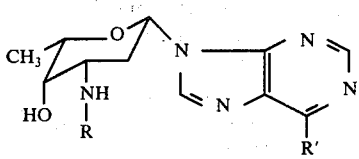

IIa R=H; R'=N(CH$_3$)$_2$ 6-dimethyl-9-(β-daunosaminyl)-adenine;
IIb R=COCH$_3$; R'=Cl protected derivative;
IIc R=COCH$_3$; R'=N(CH$_3$)$_2$ protected derivative.

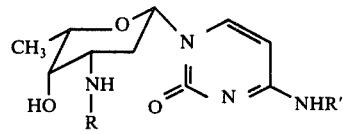

IIIa R=R'=H 1-(β-daunosaminyl)-cytosine;
IIIb R=COCF$_3$; R'=COC$_6$H$_5$, protected derivative

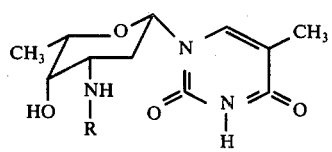

IVa R=H 1-(β-daunosaminyl)-thymine;
IVb R=COCF$_3$ protected derivative.

The above-described nucleosides of the invention display outstanding pharmacological properties, in that they have been found to synergize the antitumor activity of daunomycin and adriamycin in animal experiments (as will appear below).

The nucleosides of the invention are prepared by condensing a protected derivative of daunosamine, for example, a 3,4-diacyldaunosaminyl derivative bearing a group capable of giving up an anion in the C-1 position with a protected heterocyclic base at a temperature of from 0° to 150° C. by fusion or in the presence of an inert solvent such as chloroform, methylene dichloride, diethyl ether, benzene, toluene, acetonitrile, or nitromethane. The condensation is performed in the presence of a catalyst, for example, an inorganic salt such as mercury chloride, mercury bromide, silver carbonate or an organic acid such as chloracetic, chlorpropionic or p-toluensulfonic acid and a dehydrating agent such as a molecular sieve. The thereby obtained protected nucleosides are subsequently treated with a base such as sodium, potassium or barium hydroxide or ammonia in order to remove the protecting groups and yield the pharmacologically active free nucleoside.

The above described procedure is quite stereospecific, and leads only to the β-anomers.

According to the invention, 9-(β-daunosaminyl)-adenine is prepared by reacting, at room temperature, compound Va dissolved in methylene dichloride with N-benzoyl adenine in the presence of a molecular sieve. The resulting intermediate protected nucleoside Ib is hydrolyzed with methanolic ammonia to give the free nucleoside Ia.

6-Dimethyl-9-(β-daunosaminyl)-adenine (IIa) is prepared by fusion of fully acetylated daunosamine with 6-chloro-purine in the presence of chloracetic acid as catalyst and subsequent treatment of the reaction mixture with methanolic dimethylamine. The acetylated β-nucleoside (IIc) thus obtained is then hydrolyzed with barium hydroxide to give the free amino-nucleoside.

1-(β-Daunosaminyl)-cytosine (IIIa) and 1-(β-daunosaminyl)-thymine (IVa) are prepared by melting, under vacuum, 3,4-ditrifluoroacetyl daunosaminyl chloride (Va) respectively with bis-trimethylsilyl-N- benzoyl cytosine and bis-trimethylsilylthymine and then removing the N-protecting groups of the intermediate protected nucleosides (IIIb and IVb) by hydrolysis with methanolic ammonia.

DESCRIPTION OF THE PREFERRED EMBODIMENTS

The invention will now be illustrated in more detail by the following preparative examples.

EXAMPLE 1

9-($\beta$-daunosaminyl)-adenine (Ia)

To 1.22 g. of 3,4-ditrifluoroacetyl-daunosaminyl chloride dissolved in 50 ml. of dry methylene dichloride, 1.33 g. of benzoyl adenine and 4.3 g. of molecular sieve (4 A) were successively added. The resulting suspension was stirred for five days at room temperature. The unreacted benzoyl adenine and molecular sieve were filtered off and the methylene dichloride was evaporated off to leave a light syrup, which was refluxed for 1 hour with 50 ml. of methanol. Evaporation of the solvent left an oily residue which was purified on a silica gel column using a mixture of acetone-benzene (5:1 by volume) as eluant. By this procedure there was obtained 0.49 g. of 9-[(3'-trifluoroacetyl)-$\beta$-daunosaminyl]-benzoyl adenine (Ib); M.p. 143°–145° C.; Yield 31%. P.M.R. data (CDCl$_3$); 1.33$\delta$(d, J=6.5 Hz, CH$_3$—C(5')), 5.94$\delta$(dd, J$_{aa}$=10 Hz, J$_{ae}$=4 Hz, C(1')H), 7.30–8.10$\delta$(m, C$_6$H$_5$), 8.30 and 8.76$\delta$(two s, C(2)H and C(8)H. Mass spectrum m/e 464 (M+).

0.38 g. of this compound (Ib) were dissolved in 25 ml. of methanol and the solution was saturated at 0° C. with ammonia in a round-bottomed glass flask which was stoppered and maintained at room temperature for 1 week. The solution was then concentrated under vacuum until crystallization began and then stored overnight in a refrigerator. 0.2 g. of pure 9-($\beta$-daunosaminyl)-adenine was obtained after crystallization from isopropanol. M.p. 243°–246° C.; [$\alpha$]$_D$–8° (c=1.24 in methanol). Yield 92.5%. P.M.R. data (DMSO-d$_6$): 1.10$\delta$(d, J=6.5 Hz, CH$_3$—C(5')), 3.72$\delta$(dq, J=6.5 Hz, J'~1 Hz, C(5')H), 5.66$\delta$(dd, C(1')H, J$_{aa}$=10.5 Hz, J$_{ae}$~3 Hz), 8.15 and 8.28$\delta$(two s, C(2)H and C(8)H.

Analysis for C$_{11}$H$_{16}$N$_6$O$_2$ : C=49.99%; H=6.10%. Found: C=49.65%; H=6.18%.

EXAMPLE 2

6-Diemthyl-9-($\beta$-daunosaminyl)-adenine (IIa)

1.28 g. of 1,3,4-triacetyl daunosamine and 0.726 g. of 6-chloropurine were intimately mixed in a round-bottomed glass flask and rapidly heated at 120° C. until melting occurred. 0.015 g. of monochloracetic acid was added to the molten mixture and the flask was connected to a vacuum (0.5 mmHg). Heating was continued until the evolution of acetic acid had subsided (about 45 minutes), and then the mixture was cooled and the residue taken up in 100 ml. of chloroform. After washing with 50 ml. of saturated aqueous sodium bicarbonate solution and then with 50 ml. of 30% aqueous sodium chloride solution, the solution was evaporated to a residue.

1.6 g. of the thereby obtained 6-chloro-9-[(3'-acetyl-$\beta$-daunosaminyl)]-purine (IIb) were dissolved in 25 ml. of 40% aqueous dimethylamine, and allowed to react for 12 hours at room temperature. The reaction mixture was evaporated to a residue which was redissolved in 50 ml. of ethyl acetate. After washing with 25 ml. of a 30% aqueous sodium chloride solution, the organic phase was concentrated to a small volume and chilled. After fifteen hours, 0.77 g. of 6-dimethylamino-9-[(3'-acetyl-$\beta$-daunosaminyl)]-purine (IIc) was collected. Yield 49%. M.p. 222°–223° C. (after crystallization from ethyl acetate). P.M.R. data (CDCl$_3$): 1.30$\delta$(d, J=6.5 Hz, CH$_3$—C(5')) 2.00 $\delta$(s, CH$_3$CO), 3.53$\delta$(s, (CH$_3$)$_2$N), 5.83$\delta$(dd, J$_{aa}$=10 Hz, J$_{ae}$=4 Hz, C(1')H), 7.98 and 8.35$\delta$(two s, C(2)H and C(8)H.

Analysis for C$_{15}$H$_{22}$N$_6$O$_3$: C=53.88%; H=6.63%. Found: C=53.55%; H=6.48%.

To 2.28 g. of this compound (IIc), 115 ml. of 0.2 N barium hydroxide solution were added and the resulting mixture was heated for 20 hours at 100° C. The resulting clear solution was cooled, neutralized with excess solid carbon dioxide (dry ice) and evaporated under vacuum. The residue was extracted with hot ethanol, the inorganic salts filtered off, and the filtrate evaporated to a residue. The crude product thereby obtained was dissolved in 15 ml. of 50% aqueous methanol and placed on a column containing 75 g. of Amberlite (Trade Mark) IRC-50 ion exchange resin. The column was washed with 50% aqueous methanol until the eluate was free of ultraviolet absorbing material and then with 2 N ammonium hydroxide solution in 50% aqueous methanol. The ammonium hydroxide eluate was evaporated to afford 1.75 g. of 6-dimethyl-9-($\beta$-daunosaminyl)-adenine which was crystallized from isopropanol. Yield 88%. M.p. 232°–233° C. [$\alpha$]$_D$–4.5° (C=0.9 in methanol). P.M.R. data (DMSO-d$_6$): 1.16$\delta$(d, J=6.5 Hz, CH$_3$—C(5')), 3.46$\delta$(s, N(CH$_3$)$_2$, 3.76$\delta$(q, J=6.5 Hz, C(5')H), 5.74 $\delta$(dd, J$_{aa}$=11 Hz, J$_{ae}$=2.5 Hz, C(1')H), 8.21 and 8.30$\delta$(two s, C(2)H and C(8)H).

Analysis for C$_{13}$H$_{20}$N$_6$O$_2$: C=53.41%; H=6.89%. Found: C=53.10%, H=6.88%.

EXAMPLE 3

1-($\beta$-Daunosaminyl)-cytosine (IIIa)

A mixture of 0.5 g. of 3,4-di-trifluoroacetyl daunosaminyl chloride and 0.75 g. of 4-benzoyl-2,4-bis-trimethylsilyl-cytosine was heated at 150° C. for 1 hour in a round-bottomed glass flask connected to a water aspirator. The molten mixture was cooled and 30 ml. of 80% aqueous methanol were added thereto. The resulting suspension was then refluxed for 30 minutes. The unreacted benzoyl cytosine was filtered off and the methanolic solution was evaporated under vacuum to leave a white residue which was crystallized from methanol to give 0.13 g. of 1-[$\beta$(3'-trilfuoroacetyl-daunosaminyl)]-4-benzoyl-cytosine (IIIb). Yield 21%. M.p. 259°–261° C. [$\alpha$]$_D$–64° (c=1 in methanol). P.M.R. data (DMSO-d$_6$) at 15° : 1.22$\delta$(d, J=6.5 Hz, CH$_3$—C(5')), 5.85$\delta$(dd, J$_{aa}$=8.5 Hz, J$_{ae}$=3.5 Hz, C(1')H), 7.3–7.7$\delta$and 7.9 –8.3$\delta$(m, C(5)H, C(6)H, and aromatic protons).

0.2 g. of this protected nucleoside (IIIb) were dissolved in 60 ml. of methanol previously saturated with ammonia at 0° C. The solution was kept in a pressure flask at room temperature for a week. Then the solvent was evaporated and the residue purified by chromatography on a silica gel column using 80% aqueous methanol as the eluant. 0.105 g. of 1-($\beta$-daunosaminyl)-cytosine was obtained, which after crystallization from isopropanol had a m.p. of 152°–155° C.; yield 96%; [$\alpha$]$_D$–88° (c=1 in methanol). P.M.R. data (DMSO-d$_6$): 1.00$\delta$(d, J=6.5 Hz, CH$_3$-C(5')), 1.3–1.8 $\delta$(m, C(2')H), 5.56 δ(broad t, C(1')H), 5.72 and 7.60δ(two d, J=7.5 Hz, C(5)H and C(6)H).

Analysis calculated for $C_{10}H_{16}N_4O_3$: C=49.99%; H=6.71%; N=23.22%. Found: C=49.79%; H=6.78%; N=23.18%.

EXAMPLE 4

1-(β-Daunosaminyl)-thymine (IVa)

4.16 g. of 3,3-ditrifluoroacetyldaunosaminyl chloride and 4.74 g. of bis-trimethylsilyl-thymine were intimately mixed in a round-bottomed glass flask which was connected to a water aspirator. The mixture was heated for 45 minutes at 130° C. and the clear melt thereby obtained was cooled. 100 ml. of an 80% aqueous methanol solution were added and the resulting suspension was refluxed for 30 minutes. The unreacted thymine was filtered off and the methanolic solution evaporated to dryness. The resulting residue was extracted three times with hot methylene dichloride. The combined methylene dichloride extracts were then dried over anhydrous sodium sulphate and evaporated under vacuum to thereby obtain 2.25 g. of 1-[(3'-trifluoroacetyl)-β-daunosaminyl]-thymine (IVb), which after crystallization from ethanol had a m.p. of 247°-249°; yield 55%; $[\alpha]_D = -120°$ (c=1 in methanol). P.M.R. data (DMSO-d$_6$) at 15°: 1.18δ(d, J=6.5 Hz, CH$_3$—C(5')), 1.80δ(s, CH$_3$—C(5)), 5.72δ(dd,J$_{aa}$=10 Hz, J$_{ae}$=2Hz, C(1')H), 6.27δ(s, C(6)H).

1.13 g. of this protected nucleoside (IVb) were dissolved in 300 ml. of methanol previously saturated with ammonia at 0° C. The solution was kept at room temperature for 1 week in a well-stoppered glass flask. The solution was then concentrated to 40 ml. and poured into 250 ml. of diethyl ether. The resulting precipitate was filtered and crystallized from a 50% mixture of methol and ethanol. 0.66 g. of 1-β-daunosaminyl-thymine was obtained. Yield 80%. M.p. 266°-267° C. $[\alpha]_D$—183° (c=1 in methanol). P.M.R. data (DMSO-d$_6$): 1.13δ(d, J=6.5 Hz, CH$_3$—C(5')), 1.4-1.9δ(m, C(2')H), 1.76δ(d, J<1 Hz, CH$_3$C(5)), 3.64δ(dq, J=6.5 Hz, J~1 Hz, C(5')H), 5.50δ(dd, C(1')H, J$_{aa}$=9.7 Hz, J$_{ae}$~4 Hz), 7.60δ(q, J<1 Hz, C(5)H).

Analysis for $C_{11}H_{17}N_3O_4$: C=51.75%; H=6.71%; N=16.46%. Found: C=51.58%; H=6.77%; N=16.36%.

BIOLOGICAL ACTIVITY

Synergism Between Adriamycin and 9-(β-daunosaminyl)-adenine (Ia) and 1-(β-daunosaminyl)-cytosine (IIIa).

Tests were carried out using CD 1 female mice. The mice were injected intraperitoneally (i.p.) at day 0 with $5 \times 10^6$ cells/mouse of ascites sarcoma 180. On day 1 the mice were treated i.p. with adriamycin alone, or with adriamycin in mixture with conpounds (Ia) and (IIIa). All the compounds used in the tests were dissolved in distilled water immediately before use. The doses and the results are given in the Table.

TABLE

| Compound | (5) Dose (mg.kg.) | (1) MST (days) | (2) TC % | (3) LTS | (4) Number of Toxic Deaths Total Number of Mice |
|---|---|---|---|---|---|
| | | 13 | | 0/18 | |
| Adriamycin | 1 | 20 | 153 | 2/9 | |
| | 2 | 20 | 153 | 2/9 | |
| | 4 | 56 | 430 | 3/9 | 1/9 |
| | 8 | 49 | 377 | 3/9 | 1/9 |
| Adriamycin (1 part) plus (Ia) (9 parts) | 1 | 22 | 169 | 1/9 | |
| | 2 | 20 | 153 | 1/9 | |
| | 4 | 23 | 176 | 4/9 | |
| | 8 | 74 | 569 | 4/9 | |
| Adriamycin (1 part) plus (IIIa) (5.8 parts) | 1 | 18.5 | 142 | 1/10 | |
| | 2 | >70 | >583 | 6/10 | |
| | 4 | 23 | 176 | 4/10 | |
| | 8 | 44 | 338 | 3/9 | 1/9 |

(1) Median survival time
(2) Median survival time of treated mice/median Survival time of control mice × 100
(3) Long term survivors (> 60 days)
(4) Evaluated on the base of zooptic examinations carried out on all dead mice
(5) Adriamycin dose The data in the Table show that compounds (Ia) and (IIIa) caused in increase in the antitumor activity of adriamycin. In particular, the mixture of adriamycin (1 part) plus (Ia) (9 parts) at an adriamycin dose of 8 mg./kg. caused an increase of life span of treated mice higher than that observed after treatment with the optimal dose of adriamycin alone (4 mg./kg.). Similar data are show for treatment with 2 mg./kg. of a mixture of adriamycin (1 part) plus (IIIa) (5.8 parts).

Variations and modifications can, of course, be made without departing from the spirit and scope of the invention.

Having thus described our invention what we desire to secure by Letters Patent and hereby claim is:

1. A daunosamine nucleoside of the formula:

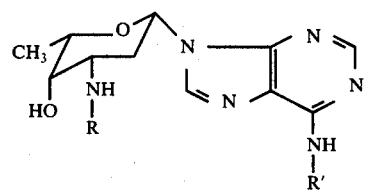

I wherein R and R' are both H or R is COCF$_3$ and R' is COC$_6$H$_5$.

2. A daunosamine nucleoside of the formula:

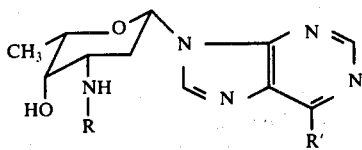

wherein R is H and R' is N(CH₃)₂; R is COCH₃ and R' is Cl or N(CH₃)₂.

3. A daunosamine nucleoside of the formula:

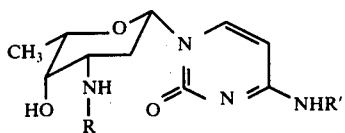

wherein R and R' are both H, or R is COCF₃ and R' is COC₆H₅.

4. A daunosamine nucleoside of the formula:

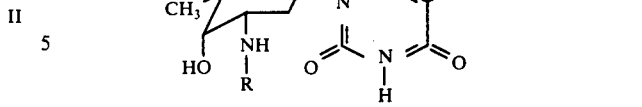

wherein R is H or COCF₃.

5. A composition comprising a therapeutically effective amount of the antitumor antibiotic daunomycin or adriamycin in combination with a synergizing amount of a daunosamine nucleoside selected from the group consisting of 9-(β-daunosaminyl)-adenine, 6-dimethyl-9-(β-daunosaminyl)-adenine, 1-(β-daunosaminyl)-adenine, 1-(β-daunosaminyl)-cytosine and 1-(β-daunosaminyl)-thymine and an inert carrier therefor.

6. A composition according to claim 5, wherein the antibiotuc is adriamycin and the daunosamine nucleoside is 9-(β-daunosaminyl)-adenine or 1-(β-daunosaminyl)-cytosine.

7. A method of inhibiting the growth of ascites sarcoma 180 which comprises intraperitoneally administering to a host afflicted with said tumor an amount of a compound selected from the group consisting of 9-(β-daunosaminyl)-adenine, 6-dimethyl-9-(β-daunosaminyl)-adenine, 1-(β-daunosaminyl)-cytosine and 1-(β-daunosaminyl)-thymine sufficient to inhibit the growth of said tumor, in combination with a therapeutically effective amount of daunomycin or adriamycin.

* * * * *

UNITED STATES PATENT OFFICE
CERTIFICATE OF CORRECTION

Patent No. 4,067,968　　　　　　　　Dated January 10, 1978

Inventor(s) Ettore Lazzari et al

It is certified that error appears in the above-identified patent and that said Letters Patent are hereby corrected as shown below:

Title page, issue date: "Jan. 10, 1977" should read -- Jan. 10, 1978 --.

Column 3, line 49: "6-Diemthyl-9-(β-daunosaminyl)-adenine (IIa)" should read -- 6-Dimethyl-9-(β-daunosaminyl)-adenine (IIa) --.

Column 4, line 68: "1.00δ" should read -- 1.08δ --.

Column 5, line 59: "methol" should read -- methanol --; line 63: "$CH_3C(5)),$" should read -- $CH_3-C(5)),$ --.

Column 6, line 43: "caused in" should read -- caused an --.

Column 8, lines 6-7 of claim 5: "1-(β-daunosaminyl)-adenine," should not be here; line 2 of claim 6: "antibiotuc" should read -- antibiotic --.

Signed and Sealed this

Eighth Day of August 1978

[SEAL]

Attest:

RUTH C. MASON
*Attesting Officer*

DONALD W. BANNER
*Commissioner of Patents and Trademarks*